United States Patent [19]

Vogel

[11] 3,985,778

[45] Oct. 12, 1976

[54] PROCESS FOR THE PURIFICATION OF CRUDE NITROANTHRAQUINONE

[75] Inventor: Axel Vogel, Cologne, Germany

[73] Assignee: Bayer Aktiengesellschaft, Leverkusen, Germany

[22] Filed: Dec. 16, 1974

[21] Appl. No.: 533,383

[30] Foreign Application Priority Data

Jan. 4, 1974    Germany............................ 2400253

[52] U.S. Cl. ............................................. 260/369
[51] Int. Cl.². ......................................... C07C 79/36
[58] Field of Search .................................... 260/369

[56] References Cited

UNITED STATES PATENTS

| | | | |
|---|---|---|---|
| 3,766,222 | 10/1973 | Hartwig et al. ..................... | 260/369 |
| 3,786,073 | 1/1974 | Frey et al........................... | 260/369 |

FOREIGN PATENTS OR APPLICATIONS

| | | |
|---|---|---|
| 2,142,100 | 2/1972 | Germany |
| 2,219,803 | 3/1973 | Germany |
| 2,200,088 | 12/1973 | Germany |

*Primary Examiner*—Arthur P. Demers
*Attorney, Agent, or Firm*—Burgess, Dinklage & Sprung

[57] ABSTRACT

The present invention relates to a process for the purification of crude 1-nitroanthraquinone in particular to a process for separating anthraquinone and 2-nitroanthraquinone from crude 1-nitroanthraquinone by treating the crude 1-nitroanthraquinone with a mixture of concentrated nitric acid and an inert organic solvent whereby a 1-nitroanthraquinone substantially free from anthraquinone and 2-nitroanthraquinone is obtained.

4 Claims, No Drawings

PROCESS FOR THE PURIFICATION OF CRUDE NITROANTHRAQUINONE

This invention relates to a process for the purification of crude 1-nitroanthraquinone from anthraquinone and 2-nitroanthraquinone.

The production of 1-nitroanthraquinone by nitrating anthraquinone is accomplished by the formation of considerable quantities of undesirable secondary products, especially 2-nitroanthraquinone and 1,5-, 1,6-, 1,7- and 1,8-dinitroanthraquinone. Also the nitration product generally contains unchanged anthraquinone.

Purification by the conventional process of fractional vacuum distillation is concerned primarily with removal of the dinitroanthraquinones. By contrast, it is not possible by this basically elegant process to separate anthraquinone and 2-nitroanthraquinone. The practical application of this process even involves considerable difficulties, especially where relatively large quantities of anthraquinone are present, because the vacuum lines are readily blocked by subliming anthraquinone.

It has now been found that anthraquinone and 2-nitroanthraquinone can be removed from 1-nitroanthraquinone containing anthraquinone and 2-nitroanthraquinone with a high degree of selectivity and with only minimal losses of 1-nitroanthraquinone, by treating 1-nitroanthraquinone containing anthraquinone and 2-nitroanthraquinone with a mixture of an inert organic solvent and concentrated nitric acid, and isolating the 1-nitroanthraquinone free from anthraquinone and 2-nitroanthraquinone in the form of a substantially insoluble product.

In the context of this invention, inert organic solvents are organic solvents of the kind which under the working conditions are largely inert with respect to the constituents of the mixture, more especially with respect to concentrated nitric acid.

Examples of solvents suitable for use in the process according to the invention are aliphatic and alicyclic hydrocarbons having up to 12 carbon atoms, preferably up to 6 carbon atoms, substituted once or several times by halogen (fluorine, chlorine, bromine, iodine), the nitro group or the sulphone group. Specific examples of such solvents include methane, ethane, propane, butane, pentane, hexane, cyclopentane and cyclohexane. In addition to the straight-chain isomers, this exemplary list naturally includes the branched isomers as well, also alkyl-substituted cycloaliphatic hydrocarbons.

It is preferred to use chlorine-substituted hydrocarbons, for example methylene chloride, chloroform, carbon tetrachloride, 1,1-dichloroethane, 1,2-dichloroethane, 1,1,2-trichloroethane, 1,1,2,2-tetrachloroethane, pentachloroethane, 1,2-dichloropropane, and 1,3-dichloropropane, 1,2,3-trichloropropane, 1,1,2,3- and 1,1,3,3-tetrachloropropane, 1,1,1,3,3-pentachloropropane, 1,1,1,2,3,3- and 1,1,1,2,2,3-hexachloropropane, 1,1,1,2,2,3,3- and 1,1,1,2,3,3,3-heptachloropropane, 1,2- and 1,4-dichlorobutane.

Examples of bromine-substituted hydrocarbons are methylene bromide, bromoform, tetrabromomethane, 1,2-dibromoethane and 1,2-dibromopropane.

It is also possible in the process according to the invention to use hydrocarbons substituted for example by fluorine or by different halogens at the same time, for example fluorotrichloromethane, difluorodichloromethane, difluorodibromomethane, 1,1,2-trifluoro-1,2,2-trichloroethane and perfluoro-1,3-dimethyl cyclohexane.

Among the hydrocarbons substituted by the nitro group, reference is made in particular to nitromethane and nitroethane.

Among the hydrocarbons substituted by the sulphone group, reference is made in particular to dimethyl sulphone and tetramethylene sulphone.

It is of course also possible to use mixtures of different organic solvents.

In the context of the invention, concentrated nitric acid is nitric acid containing at least 75% by weight of $HNO_3$, preferably at least 90% by weight of $HNO_3$ and, in particular, about 98% by weight of $HNO_3$.

The water content of the solution mixture is generally selected so that the ratio of nitric acid to water, expressed in parts by weight, is at least 75:25, preferably at least 90:10 and, in particular, about 98:2.

The quantity and composition of the solvent mixture may be varied within very wide limits.

In general, from 1 to 20 mols, preferably from 2 to 10 mols and, in particular, from 3 to 6 mols of concentrated nitric acid are used per mol of anthraquinone and 2-nitroanthraquinone. The concentrated nitric acid is used in the form of a 1 to 35% by volume mixture, preferably in the form of a 2 to 20% by volume mixture and, in particular, in the form of a 3 to 15% by volume mixture with the inert organic solvent.

Where the at least 90% by weight nitric acid is used, it is preferred to use from 2 to 10 mols of nitric acid per mol of anthraquinone and 2-nitroanthraquinone in the form of a 1 to 35% by volume mixture with the inert organic solvent. Where approximately 98% by weight nitric acid is used, it is preferred to use from 2 to 10 mols and more especially from 3 to 6 mols of nitric acid per mol of anthraquinone and 2-nitroanthraquinone in the form of a 3 to 15% by volume mixture with the inert organic solvent.

In addition to the nitric acid, the solution mixture may contain other mineral acids which are substantially immiscible with the organic solvent, preferably the mineral acids used for nitration of the anthraquinone, for example sulphuric acid, phosphoric acid or hydrofluoric acid, or even strong organic acids for example, alkane sulphonic acids and their acid or neutral salts. The quantity in which these additional acids may be present is generally determined by the reaction conditions prevailing during nitration of the anthraquinone to form the crude 1-nitroanthraquinone. The water content of the mineral acid phase should be such that it does not give rise either to undesirably heavy extraction of the nitric acid from the organic solvent or to appreciable further nitration of the 1-nitroanthraquinone.

The process according to the invention is preferably carried out by mixing 1-nitroanthraquinone containing anthraquinone and 2-nitroanthraquinone, of the kind obtained for example by the nitration of anthraquinone, with the organic solvent, preferably without intermediate isolation in the presence of the nitration medium, optionally adjusting the concentration of the mineral acid to the optimum value and dissolving substantially all the anthraquinone and 2-nitroanthraquinone by the addition of concentrated nitric acid. The undissolved 1-nitroanthraquinone substantially free from anthraquinone and 2-nitroanthraquinone is then separated off, for example by filtration, decantation or centrifugation, optionally washed with a little inert organic solvent and/or water and then dried.

The inert organic solvent and, optionally, the concentrated nitric acid as well may be recovered from the mother liquor containing anthraquinone and 2-nitroanthraquinone by subjecting the mother liquor for example to fractional distillation. However, the dissolved solids may also be precipitated from the mother liquor by extracting the nitric acid from the mother liquor or destroying it, for example by the addition of readily nitratable aromatic compounds, such as phenols, naphthols, thionaphthols and their homologues, toluene, oxylene or naphthalene, or with particular advantage by washing the nitric acid, preferably with water. However, basically reacting compounds may also be used for washing either as such or in solution, for example in water. Examples of suitable basically reacting compounds are alkali and alkaline-earth metal hydroxides such as sodium hydroxide, potassium hydroxide or calcium hydroxide, or their anhydrides such as calcium oxide, the acid and neutral salts of carbonic acid, more especially sodium bicarbonate, sodium carbonate, potassium carbonate, calcium carbonate and barium carbonate, or aliphatic or aromatic amines such as triethylamine, triethanolamine or pyridine.

However, it is also possible to use the mother liquors for the production of 1-nitroanthraquinone or dinitroanthraquinone, optionally following the addition of more anthraquinone, by nitration in the presence of the inert organic solvent.

The process according to the invention is generally carried out at a temperature in the range from −30° to +70° C, preferably at a temperature in the range from 0° to 50° C and more especially at about room temperature. The pressure can be varied within wide limits, the process preferably being carried out under normal pressure or under elevated pressure.

The 1-nitroanthraquinone isolated is substantially free from anthraquinone and 2-nitroanthraquinone and, in this form, is particularly suitable for the separation of any dinitroanthraquinones present by fractional vacuum distillation.

The process according to the invention may be carried out in batches, for example in a vessel equipped with a stirrer, or even continuously, for example in a column, recirculation plant, in a cascade of vessels or similar apparatus.

The process according to this invention offers a number of significant advantages over conventional processes. Thus, a 1-nitroanthraquinone substantially free from anthraquinone and 2-nitroanthraquinone can be obtained simply and economically from a 1-nitroanthraquinone containing anthraquinone and 2-nitroanthraquinone. Another particular advantage of the process according to the invention is that the anthraquinone and 2-nitroanthraquinone can be seperated off in the presence of the nitration medium and, hence, without intermediate isolation of the crude 1-nitroanthraquinone. In addition, the 1-nitroanthraquinone obtained by the process according to the invention accumulates in such a form that further purification, for example by fractional vacuum distillation, can be carried out particularly easily and effectively. Finally, the filter times are considerably shortened in relation to the prior art by virtue of the low viscosity of the mother liquors, whilst filtration can be carried out on a large scale.

1-Nitroanthraquinone is a commercial-grade intermediate product which is used, for example, for the production of 1-aminoanthraquinone which is an important intermediate product for numerous anthraquinone dyes.

EXAMPLE 605 g of crude 1-nitroanthraquinone with the following composition: 77% by weight of 1-nitroanthraquinone, 2.1% by weight of anthraquinone, 6.9% by weight of 2-nitroanthraquinone, 2.9% by weight of 1,5-dinitroanthraquinone, 2.9% by weight of 1,6-dinitroanthraquinone, 3.1% by weight of 1,7-dinitroanthraquinone, 2.5% by weight of 1,8-dinitroanthraquinone and 2% by weight of oxynitroanthraquinones (obtained by nitrating anthraquinone with nitric acid in conventional manner), were suspended at 20° C in a mixture of 800 ml of methylene chloride and 46 ml of 98% by weight nitric acid. The mixture was stirred for 1 hour and then poured on to a filter. The filter residue was washed first with 400 ml of methylene chloride and then with water until it was neutral. The dry yield amounted to 474 g. The product contained 90% by weight of 1-nitroanthraquinone, 0.25 % by weight of anthraquinone, 0.25% by weight of 2-nitroanthraquinone, 3.5% by weight of 1,5-dinitroanthraquinone, 0.6% by weight of 1,6-dinitroanthraquinone, 2.9% by weight of 1,7-dinitroanthraquinone and 2.4% by weight of 1,8-dinitroanthraquinone.

What we claim is:

1. A process for separating anthraquinone and 2-nitroanthraquinone from crude 1-nitroanthraquinone containing anthraquinone and 2-nitroanthraquinone which comprises adding to the crude 1-nitroanthraquinone a mixture consisting essentially of concentrated nitric acid content of at least 90% by weight and an inert organic solvent selected from the group of aliphatic and alicyclic halogenated hydrocarbons, wherein from 1 to 20 moles of concentrated nitric acid is employed per mole of combined amount of anthraquinone and 2-nitroanthraquinone in the form of a 1–35% by volume mixture with said organic solvent, and separating off the insoluble 1-nitroanthraquinone.

2. A process as claimed in any of claim 1, wherein from 2 to 10 mls of approximately 98% nitric acid per mol of anthraquinone and 2-nitroanthraquinone are used in the form of a 2 to 20% by volume.

3. A process as claimed in claim 2, wherein from 3 to 6 mols of approximately 98% nitric acid are used per mol of anthraquinone and 2-nitroanthraquinone.

4. A process as claimed in claim 2, wherein the nitric acid is used in the form of a 3 to 15% by volume mixture with the organic solvents.

* * * * *